United States Patent [19]

Cain

[11] 4,199,865
[45] Apr. 29, 1980

[54] ORTHODONTIC SPRING APPLIANCE AND ASSEMBLY

[76] Inventor: Steve B. Cain, 11006 NW. 58th St., Parkville, Mo. 64152

[21] Appl. No.: 796,987

[22] Filed: May 16, 1977

[51] Int. Cl.² .............................................. A61C 7/00
[52] U.S. Cl. ...................................... 433/21; 267/168
[58] Field of Search ............. 32/14 A, 14 D; 267/168, 267/92, 179; 254/10.5

[56] References Cited

U.S. PATENT DOCUMENTS

| 783,609 | 2/1905 | Canning | 32/14 A |
|---|---|---|---|
| 1,199,663 | 9/1916 | Canning | 32/14 A |
| 1,202,797 | 10/1916 | Canning | 32/14 A |
| 1,202,798 | 10/1916 | Canning | 32/14 A |
| 1,452,436 | 4/1923 | Pullin | 267/168 |
| 1,562,403 | 11/1925 | Wilson | 267/179 |
| 1,622,106 | 3/1927 | Hallwood | 267/168 |
| 2,320,331 | 5/1943 | Jenewein et al. | 267/179 |
| 3,618,214 | 11/1971 | Armstrong | 32/14 A |
| 3,936,938 | 2/1976 | Northcutt | 32/14 A |

FOREIGN PATENT DOCUMENTS 2311225  12/1976  France ..................... 267/168

Primary Examiner—Louis G. Mancene
Assistant Examiner—John J. Wilson
Attorney, Agent, or Firm—Lowe, Kokjer, Kircher, Wharton & Bowman

[57] ABSTRACT

An intra-oral orthodontic spring appliance is provided which consists of a metallic coil spring having an enlarged tension releasable means at one end which engages fixed spring mounting means in the mouth and a tail at the other end which engages suitable means on a tooth to be repositioned. Preferably, the enlarged tension releasable means is an open coil spring formed over a portion of a closed coil spring. When the closed coil spring is passed through a fixed spring mounting means, e.g., a buccal tube, and attached to a tooth to be repositioned, the retractive force is provided by compression of the open coil spring and expansion of the closed coil spring.

4 Claims, 4 Drawing Figures

ORTHODONTIC SPRING APPLIANCE AND ASSEMBLY

BACKGROUND OF THE INVENTION

The invention described herein relates to orthodontic appliances and their use is the practice of orthodontics. More specifically, it relates to coiled wire springs which may easily be prefabricated and which are rapidly and easily installed in the mounth to correct malocclusions of teeth. In orthodontics it is frequently necessary to move teeth along the jaw so as to assure proper spacing and correct malocclusions. This movement is termed retraction. Retraction of individual teeth in orthodontic treatment is accomplished by various mechanisms and techniques. The ideal retraction mechanism would be one that applies a force no greater than the capillary pressure of the peridontal membrane. No practical force mechanism is available that creates a constant force of this minute magnitude. However, it is generally accepted that the bodily retraction of a tooth without severe loss of anchorage is best accomplished with light forces.

The design of fixed orthodontic appliances and the oral environment combine to restrict the retraction mechanisms to a limited number of forms or techniques. One important restriction is the distance over which the activated retraction mechanism can provide the requisite retraction force. Ideally, a single activation would retract an individual tooth the total required distance with a continuous light force. In actual practice it has heretofore been difficult to apply the necessary force in anything approaching a constant manner. Other important considerations in the design of retraction mechanisms are the ease of placement and removal and the ability to withstand the forces of mastication without breakage or deformation. An additional consideration is the desirability of eliminating patient responsibility for activation or placement of the mechanism. Finally, it should be an intra-oral device.

Prior art intra-oral retraction mechanisms include closed coil metallic springs, open coil metallic springs, and elastic materials. Elastic bands of certain rubbers or plastics have several advantages insofar as they can be inserted and removed by the patient, do not have to be cleaned because they are disposable, and do not have to be reactivated by the orthodontist. Unfortunately, they also have a number of rather severe disadvantages. The fact that they can easily be removed by the patient at will serves to frustrate the orthodontist's efforts if they are in fact prematurely removed. More importantly, presently used elastic materials are subject to interaction with the natural fluids in a patient's mouth. This interaction rapidly degrades the physical properties of the conventional strand elastics, resulting in a tensile force reduction of about 40% after the elastics have been in place for only a few hours. Accordingly, the restoring force exerted by the elastic when stretched to a specific elongation does not remain constant and is difficult to control. For this reason, elastic bands require freqent replacement.

Closed coil springs of metal wire are used as retraction mechanisms by attaching them in tension between a fixed anchor point in the mouth and the tooth desired to be moved. The tension expands or opens the coils of the spring and the retractive force is produced by the coils attempting to close to the rest position. It will be apparent that as the retracting tooth moves, the coils approach nearer to the rest position and, as a result, the force acting on the tooth is reduced.

Open coil springs operate just the reverse of closed coil springs. In operation, they are placed in compression so that the coils supply a retractive force by attempting to move back to the open, rest position. As a practical matter, open coil springs are not as frequently used for retraction although some orthodontists do use them for this purpose.

The standard closed coil retracting springs have straight wires at either end which are used to mount them to brackets on an anchor tooth and the tooth to be retracted. Tying these ends to the brackets is often a difficult procedure, especially in the back of the mouth. Frequently, it is time consuming. Removal is also time consuming, requiring in the usual practice that the spring coils be cut and the ends then unwrapped from the brackets on the teeth. In the back of the mouth this unwrapping may inadvertently result in puncture wounds in the cheek or gum because the wire is normally of small diameter and readily penetrates tissue. In any case, the process is normally uncomfortable to the patient.

It will be apparent that it is highly desirable to minimize or avoid tying or wrapping procedures altogther—particularly in the back of the mouth—while at the same time assuring that the retracting spring is not capable of being readily removed by the patient.

In U.S. Pat. No. 3,936,938 for "Orthodontic Spring Appliance and Spring Clip Therefor" issued on Feb. 10, 1976, the inventor discloses apparatus for avoiding the wrapping problem. In this apparatus, at least one end of the retraction spring has a straight extension having protrusions thereon spaced at predetermined intervals. The wire with protrusions may readily be connected to a spring clip which may be attached to the arch wire or a tooth bracket. The clip has a slot therein which is so designed that it readily accommodates the protrusion but prevents the wire from being pulled out by the tension force of the spring. It should be noted that the spring appliance of U.S. Pat. No. 3,936,938 requires the use of a special spring clip which appears to have no utility other than as an anchor point for the retraction spring. Further, spring clips of the type disclosed in this patent are subject to occasional inadvertent release of the spring. They also permit the patient to easily release the spring. In either instance, the purpose of the orthodontist is nullified.

SUMMARY OF THE INVENTION

In its broad sense, the present invention encompasses an orthodontic treatment assembly for applying repositioning forces to teeth in a patient's mouth comprising in combination (a) means suitable for insertion in the mouth to produce a tension force, this tension producing means comprising a metallic wire closed coil spring having at one end a tail and at the other end enlarged tension releasable means for holding the coil spring in engagement with fixed spring mounting means, (b) fixed spring mounting means for engaging the enlarged tension releasable means on the coil spring, and (c) means on a tooth to be repositioned for engaging the tail portion of the coil spring when the coil spring is in tensioned engagement with the spring mounting means, thereby applying a desired directed repositioning force on the tooth. The spring is readily removed from the fixed spring mounting means by exerting a tension on it substantially in excess of that required for the retraction, thereby causing the tension releasable means to deform and pass through the spring mounting means.

In a preferred embodiment, the tension releasable means is an open coil of spring wire formed over a portion of the closed coil and the fixed spring mounting means is a buccal tube attached to an anchor tooth. The diameter of the buccal tube is such that the closed coil of the spring easily passes therethrough but the open coil does not. The open coil thus serves to hold the spring in place in the buccal tube when tension is applied to the spring. When tension is applied, the closed coil expands and the open coil compresses, thereby providing a double action retraction coil spring. The spring is easily removed from the buccal tube by exerting a firm pull on the tail which exceeds the proportional limit of the spring. This causes the enlarged coil to deform and permits it to pass through the tube.

Description of the Preferred Embodiments

Figure 1:
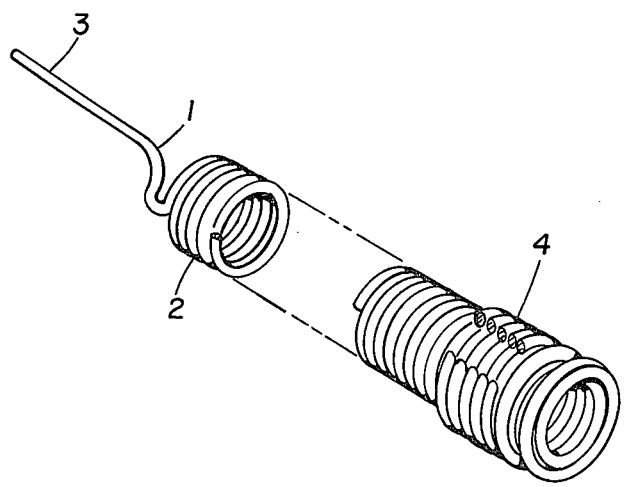
FIG. 1 is a view of one embodiment of the spring appliance of this invention.

In this invention, the working forces for the orthodontic device are provided by coil wire springs. When the springs are installed in the mouth, the resulting forces on the maloccluded teeth are determined by the characteristics of the static springs and by the extent of spring elongation in one embodiment and by the combination of elongation and compression in another embodiment.

Selection of wire type and diameter and of coil configuration is important in the manufacture of all embodiments. Spring tempered stainless steel wire stock is commercially available with satisfactory strength and elastic properties. Knowing the basic physical properties of a particular wire, the determination of spring parameters such as wire diameter, number of coils, and coil diameter is readily made by referring to any of the standard texts on spring design.

To be functional and comfortable, the coil springs of this invention should have a sufficiently small outside diameter so that they can be accommodated in the limited space available in the vestibules of the mouth. Moreover, the springs should also be available in various lengths to permit use in a variety of positions and to accommodate the wide ranges of intermaxillary spans in the mouths of different patients. Appliance length is readily determinable because other parameters such as wire diameter, cross section, and material, coil diameter, and the number of springs can be varied to provide a spring having the desired unelongated or static length and a desired working elongation.

A critical feature of the present invention is the use with a closed coil spring of anchor means positioned to hold the spring in fixed relation to appropriate fixed spring mounting means when the spring is activated to the desired tension. Typically, such fixed spring mounting means is attached directly to an anchor tooth but this need not automatically be the case. Thus, it could be attached to the arch wire at an appropriate point. The anchor means is tension releasable, i.e., it releases from and passes through the mounting means when sufficient force is applied to the closed coil spring. This permits the orthodontist or a technician acting under his direction to easily remove the spring from the mounting means merely by firmly pulling on the spring. In one embodiment of the invention, the anchor means is an enlarged closed coil of the spring wire formed at the end of the closed coil spring. Preferably, this enlarged anchor coil is formed over a portion of the closed coil spring. The diameter of this outer closed anchor coil is sufficiently large that it engages the mounting means firmly while yet permitting the closed coil spring to pass therethrough.

In another embodiment, which is the preferred embodiment, the anchor coil consists of an open coil spring which is compressed when the closed coil spring is elongated and thus serves to produce a retractive force along with that resulting from the elongation of the closed coil spring. This latter embodiment is conveniently characterized as a double action retraction coil spring. It will be readily apparent that such a double action spring permits the necessary retractive force to be achieved over a shorter elongation distance for the closed coil spring. This, in turn, permits a more constant force to be placed on the retracting tooth for a longer period of time, thereby allowing better retraction with less need for adjustment of the tension on the spring.

Figure 4:
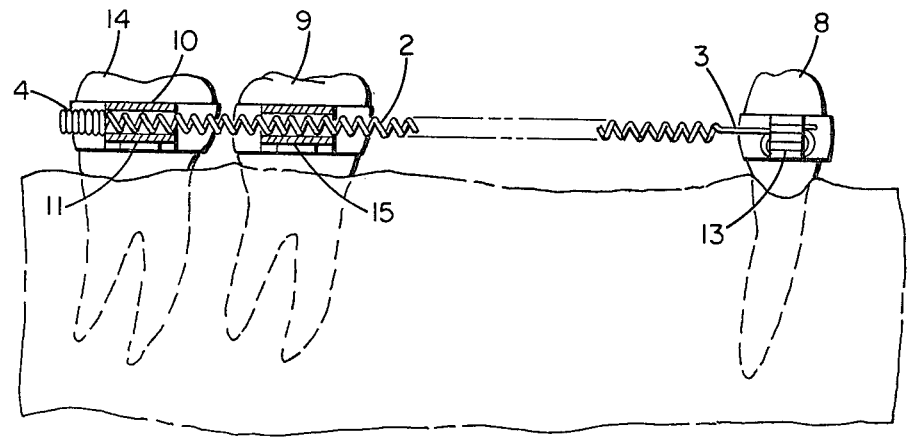
FIG. 4 is a view of the orthodontic assembly of the invention showing the use of the spring appliance in a limited working space.

Another substantial advantage of the present invention over the teaching of the prior art is that it permits retractions in limited working volumes such as that shown, for example, in FIG. 4. Prior art coil springs are designed to be placed in a region located adjacent the spacing between the teeth involved. With the present invention, however, a goodly portion of the spring is located adjacent to the anchor tooth because it passes through the mounting means positioned on the side of the anchor tooth.

With appropriate modification, the spring clips disclosed in U.S. Pat. No. 3,936,938 may be used as the rear mounting means for the retraction spring. U.S. Pat. No. 3,936,938 is hereby incorporated by reference into this application. Preferably, however, a variety of commercially available buccal tubes, e.g., headgear tubes, twin-wire tubes, lightwire tubes, and the multiphase maxillary and mandibular tubes, may conveniently be used for this purpose. It can be seen that the use of buccal tubes is advantageous in that such tubes serve to protect a substantial portion of the closed coil spring. It does not matter whether the cross section of the buccal tube is circular or square, provided that the diameter of the tube is sufficient to permit the inner closed coil portion of the spring to pass readily therethrough while at the same time preventing the outer anchor coil from so doing.

The spring may be easily attached to the tooth to be retracted by wrapping a straight wire extension or tail from the spring coil around a bracket on this tooth. This is a technique well known and commonly used in the orthodontic art. See, e.g., FIG. 3. Alternatively, spring clips and spring tails of the type taught in U.S. Pat. No. 3,936,938 may be used for this purpose.

One embodiment of the spring appliance of the invention is shown in FIG. 1. The appliance consists of a single strand of spring-tempered wire 1 formed into a closed coil 2 having a straight extension or tail 3 at one end and a closed anchor coil 4 at the other end. The number of turns in anchor coil 4 may be varied. There must be a minimum number of turns sufficient to prevent deformation and release from the mounting means as a result of the combination of the retracting tension and any other forces which may normally be applied to the spring during, for example, mastication of food. On the other hand, there should not be an undue number of turns such that an excessive force is required to deform the anchor coil so that it readily passes through the mounting means 10 (see FIG. 3) when the retraction spring is removed from the mouth. By the term "turn" is meant one 360° revolution of the spiral of wire which forms anchor coil 4.

Figure 2:
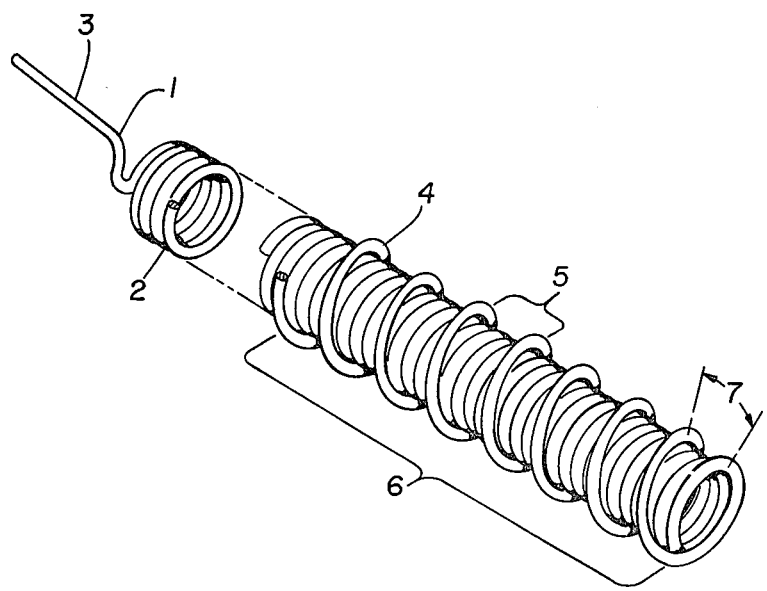
FIG. 2 is a view of a preferred embodiment of the spring appliance of the invention.

A preferred embodiment of the spring appliance of the invention is shown in FIG. 2. This appliance is substantially similar to that of FIG. 1 except that anchor coil 4 is open 5 rather than closed and thus serves as an open coil spring 6 to provide certain of the retracting force on tooth 8 to be retracted (see FIG. 3). The embodiment of FIG. 2 is thus a double action retraction coil spring. It will be readily apparent that the retractive force provided by open coil spring 6 depends, among other things, on the diameter of the coil, the number of turns, and the angle 7 of the spiral.

Figure 3:
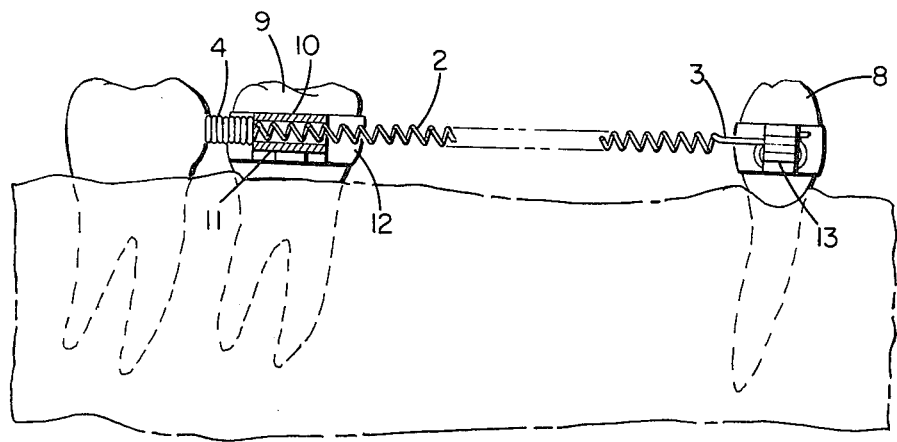
FIG. 3 is a partially cut-a-way view of the orthodontic assembly of the invention.

FIG. 3 shows the manner in which the spring appliance of the invention is used. In FIG. 3, mounting means 10 is a buccal tube 11 attached to band 12 on anchor tooth 9, but as has been indicated previously in this specification it could as easily be a spring clip of the type disclosed in U.S. Pat. No. 3,936,938 modified to permit the passage of coil 2 therethrough. The appliance is activated as follows. The tail 3 of the spring is passed through buccal tube 11 from the distal to the mesial end, i.e., from the end of the tube furthest from the tooth 8 to be retracted to the end closest to that tooth. Coil 2 is pulled through tube 11 until anchor coil 4 butts against the distal end of tube 11. Buccal tube 11 thus holds coil 2 in place and protects a substantial portion of it from deformation. The spring appliance is activated by pulling on tail 3 to extend closed coil 2. If the embodiment of FIG. 2 is used, this pull simultaneously compresses open coil 6 which is also serving as anchor coil 4. When the desired force is present, the tail 3 is attached to the tooth 8 desired to be retracted in such manner that this force is then maintained on that tooth. This is easily accomplished by wrapping tail 3 around a bracket 13 on tooth 8 and snipping off the excess.

When the retraction is complete or when another spring is desired to be used, the spring in place is readily removed by cutting tail 3 near coil 2 and then pulling the spring forward through tube 11 with a force sufficient to exceed its proportional limit. This causes anchor coil 4, which heretofore had been holding the spring in place in tube 11, to uncoil into and through the tube 11. The remaining portion of tail 3 is quickly and easily unwrapped from bracket 13 on tooth 8.

The scope of the invention is as set forth in the Summary of the Invention and the appended claims and is not limited to the specific embodiments described herein. Such embodiments are merely illustrative of the best mode contemplated for the performance of the invention.

What I claim is:

1. A double action retraction coil spring useful for providing a substantially steady work force on a tooth to be retracted which comprises a single strand of spring tempered wire formed into a closed first coil having at one end a tail and at the other end an enlarged open second coil, said second coil formed over at least a portion of said first coil, and said tail being adapted to be affixed to said tooth to provide the desired work force on said tooth when said spring is activated.

2. An orthodontic treatment assembly for applying repositioning forces to teeth in a patient's mouth comprising in combination (a) means suitable for insertion in the mouth to produce a tension force, said tension producing means being an integral unit formed from a single continuous strand of metallic wire and comprising a closed coil spring having at one end a tail and at the other end an enlarged tension releasable open coil spring having a diameter larger than that of said closed coil spring and formed over a portion of said closed coil spring for holding said closed coil spring in engagement with fixed spring mounting means, (b) fixed spring mounting means for engaging said open coil spring, and (c) means on a tooth to be repositioned for engaging the tail portion of said closed coil spring when said closed coil spring is in tensioned engagement with said spring mounting means, thereby applying a desired directed repositioning force on said tooth.

3. The orthodontic treatment assembly of claim 1 wherein said closed coil spring passes through said fixed spring mounting means.

4. The orthodontic treatment assembly of claim 3 wherein said fixed spring mounting means is a buccal tube fixed to an anchor tooth.

* * * * *